United States Patent [19]

Burleigh et al.

[11] Patent Number: 4,734,184
[45] Date of Patent: Mar. 29, 1988

[54] SELF-ACTIVATING HYDRATABLE SOLID-STATE ELECTRODE APPARATUS

[75] Inventors: Peter Burleigh; Bruce Burgess; Ricky Hendershot, all of Ann Arbor, Mich.

[73] Assignee: Diamond Sensor Systems, Inc., Ann Arbor, Mich.

[21] Appl. No.: 21,520

[22] Filed: Feb. 26, 1987

Related U.S. Application Data

[63] Continuation of Ser. No. 770,697, Aug. 29, 1985, abandoned.

[51] Int. Cl.$^4$ .............................................. G01N 27/46
[52] U.S. Cl. ..................................... 204/409; 204/1 T; 204/411; 204/415; 204/433; 128/635
[58] Field of Search ............... 204/1 T, 403, 409, 411, 204/415, 433; 128/635

[56] References Cited

U.S. PATENT DOCUMENTS

| | | | |
|---|---|---|---|
| 3,999,284 | 12/1976 | Bicher | 29/570 |
| 4,197,853 | 4/1980 | Parker | 128/635 |
| 4,214,968 | 7/1980 | Battaglia et al. | 204/418 |
| 4,486,291 | 12/1984 | Schindler et al. | 204/415 |
| 4,492,622 | 1/1985 | Kuypers | 204/403 |
| 4,534,356 | 8/1985 | Papadakis | 128/635 |
| 4,536,274 | 8/1985 | Papadakis et al. | 204/433 |

OTHER PUBLICATIONS

International Application WO85/02257, published May 23, 1985.

Primary Examiner—T. Tung
Attorney, Agent, or Firm—Krass & Young

[57] ABSTRACT

This invention relates to solid-state electrode or microelectrode sensor apparatus for measuring certain characteristics of an aqueous sample such as a body fluid or a blood sample and more particularly to such apparatus which employs a disposable cartridge containing a sensor or a bank of sensors for such characteristics and reagents used to calibrate the sensors.

5 Claims, 13 Drawing Figures

SELF-ACTIVATING HYDRATABLE SOLID-STATE ELECTRODE APPARATUS

This is a continuation of co-pending application Ser. No. 770,697 filed on Aug. 29, 1985 now abandoned.

FIELD OF THE INVENTION

This invention relates to solid state electrode or sensor apparatus for measuring certain characteristics of an aqueous sample such as a body fluid or a blood sample and more particularly to such apparatus which employs a disposable cartridge containing a sensor or a bank of sensors for such characteristics and reagents used to calibrate the sensors.

BACKGROUND OF THE INVENTION

In a variety of clinical situations it is important to measure certain chemical characteristics of the patient's blood such as pH, concentrations of calcium, potassium ions and hematocrit, the partial pressure of $O_2$ and $CO_2$ and the like. (See, for example, Fundamentals of Clinical Chemistry, Tietz, Editor, page 135 et seq., Electrochemistry; page 849 et seq., Blood Gases and Electrolytes; 1976, Saunders Company, Phila.; see also the patent to Battaglia et al. U.S. Pat. No. 4,214,968.) These situations range from a routine visit of a patient in a physician's office to monitoring during open-heart surgery. The required speed, accuracy, and similar performance characteristics vary with each situation.

Measurement of chemical characteristics of blood during open-heart surgery provides the most demanding set of criteria. Presently, blood gas analysis during major surgery is provided by repeated transfer of discrete blood samples to a permanent lab-based blood gas analyzer or by use of sensors placed in-line with the extra-corporeal blood circuit of a heart-lung machine employed to bypass the patient's heart.

The transfer of discrete blood samples, required by blood-gas analyzers inherently increases the risk of contaminating the blood sample with ambient air, which may alter certain of the monitored characteristics. Additionally, since such analyzers are complex and costly devices, they are typically located only in the hospital lab where they need to be operated by a skilled technician, resulting in undesirable delay during surgery, critical care or intensive care. Further, such analyzers employ bubble tonometers to generate a suitable gas reference mixture by dissolving quantities of gases, stored in pressurized free-standing tanks, into the electrolyte solution. While replacement of these gas tanks is infrequently required, it is a cumbersome procedure. Finally, these existing analyzers require cleaning to decontaminate all exposed portions from the prior patient's blood prior to subsequent use.

Although use of in-line sensors minimizes both the risk of contamination during transfer and the risk of delay, these sensors have a response which normally varies or "drifts" during use; moreover, this drift is not at a constant rate. Present in-line sensors can only be calibrated before they are placed in the extracorporeal circuit. Thus, the inherent drift of these in-line sensors cannot be monitored, resulting in readings of ever decreasing reliability as time passes.

SUMMARY OF THE INVENTION

The present invention is directed to a system which provides quick, on-site contemporaneous blood chemistry analysis, with minimal risk of contamination, and which maintains its accuracy over its useful life. The system can be operated in an automatic sampling mode presently to be described in detail and also a discrete sampling mode. Thus, for example, the system can be operated in the automatic mode sampling the extracorporeal blood flow of a patient following which, after automatic sampling is discontinued, discrete samples of the patient's blood can be taken.

While these characteristics are desirable in machines for use in a wide variety of applications, a blood chemistry analysis machine forming a preferred embodiment of the present invention is adapted to be connected to an extracorporeal shunt or an ex vivo blood source such as a heart/lung machine used to sustain a patient during surgery, intensive care, critical care and the like, to allow small test samples of flowing live ex vivo blood to be diverted off-line from either the venous or arterial flow lines of the heart/lung machine directly in real time to a chamber exposed to a bank of solid-state micro-electrodes which generate electrical signals proportional to chemical characteristics of the real time flowing blood sample.

The bank of electrodes is housed in a disposable cartridge, adjacent to a thermal plate which maintains the test sample at a constant temperature. Upon insertion of the cartridge into a suitably adapted blood chemistry analysis machine, the electrodes connect to an electrode interface which selects one of the plurality of electrical signals generated by the sensors and passes the selected signal to a microprocessor in the machine where it is converted from analog to digital form suitable for analysis, storage and display.

A metal plate in the cartridge connects to a thermal unit in the machine which monitors the temperature of and generates and transmits heat to the plate and through it to the sample in the adjacent electrode chamber in order to maintain the sample at a constant temperature.

The cartridge also contains at least one, and preferably two containers of reference or calibrating electrolyte solution (i.e., solution serving for purposes of quality control including calibration, sometimes referred to hereinafter as calibration solution), as well as a reservoir suitable to collect waste fluids following assay. Upon insertion of the cartridge, a selection valve in the cartridge connects to a shaft in the machine, controlled by the microprocessor, to selectively allow either of the calibrating solutions or the test sample to flow across the electrodes.

The force driving the fluid flow through the cartridge is provided by a peristaltic pump formed when a set of rotatable drive rollers in the machine pinch exposed portions of tubing against the curved wall of the pump slot on the cartridge. The rotation of the rollers forces either the calibrating solutions or a test sample from their respective sources through the cartridge tubing across the electrode chamber and into the waste collection reservoir. The rotation of the drive rollers is controlled by the microprocessor.

In addition to the features already mentioned, the analysis machine houses an internal digital clock which provides a time base for the operation of the system, a back-up battery power source, an operator keyboard, a display and a printer.

In operation, after all connections are suitably made, the selection valve and drive rollers cooperate to cause the calibrating solution to flow into the electrode chamber where a reading is taken and stored in the microprocessor. Subsequently and in a similar manner, a reading of the test sample is taken, analyzed by the microprocessor and displayed. The assayed fluids are directed into the waste collection reservoir. The microprocessor controls and repeats this cycle of calibration and test sample assay at a rate preselected and entered by the operator through the control keyboard. The keyboard also allows the operator to take an immediate assay at any time, even while the machine is in its automatic cycle mode, limited only by the recycling time of between two and three minutes. Following surgery, the cartridge and the tubing connecting the venous and arterial flows of the heart-lung machine to the cartridge are discarded and the machine is ready for use with a new cartridge.

BRIEF DESCRIPTION OF THE DRAWINGS

Advantages of the present invention will be apparent upon reading the following specification and by reference to the drawings in which:

FIG. 8b is a cross sectional view of this electrode card taken on line 8b—8b of FIG. 8a;

DETAILED DESCRIPTION OF THE INVENTION

A preferred embodiment of the invention is adapted to measure the unbound concentration, or activity, of two blood gases, oxygen and carbon dioxide, of two ions, potassium and calcium, and of the blood pH and hematocrit. Alternative embodiments of the invention measure selected ones of these blood characteristic factors and/or other additional factors.

Figure 1:
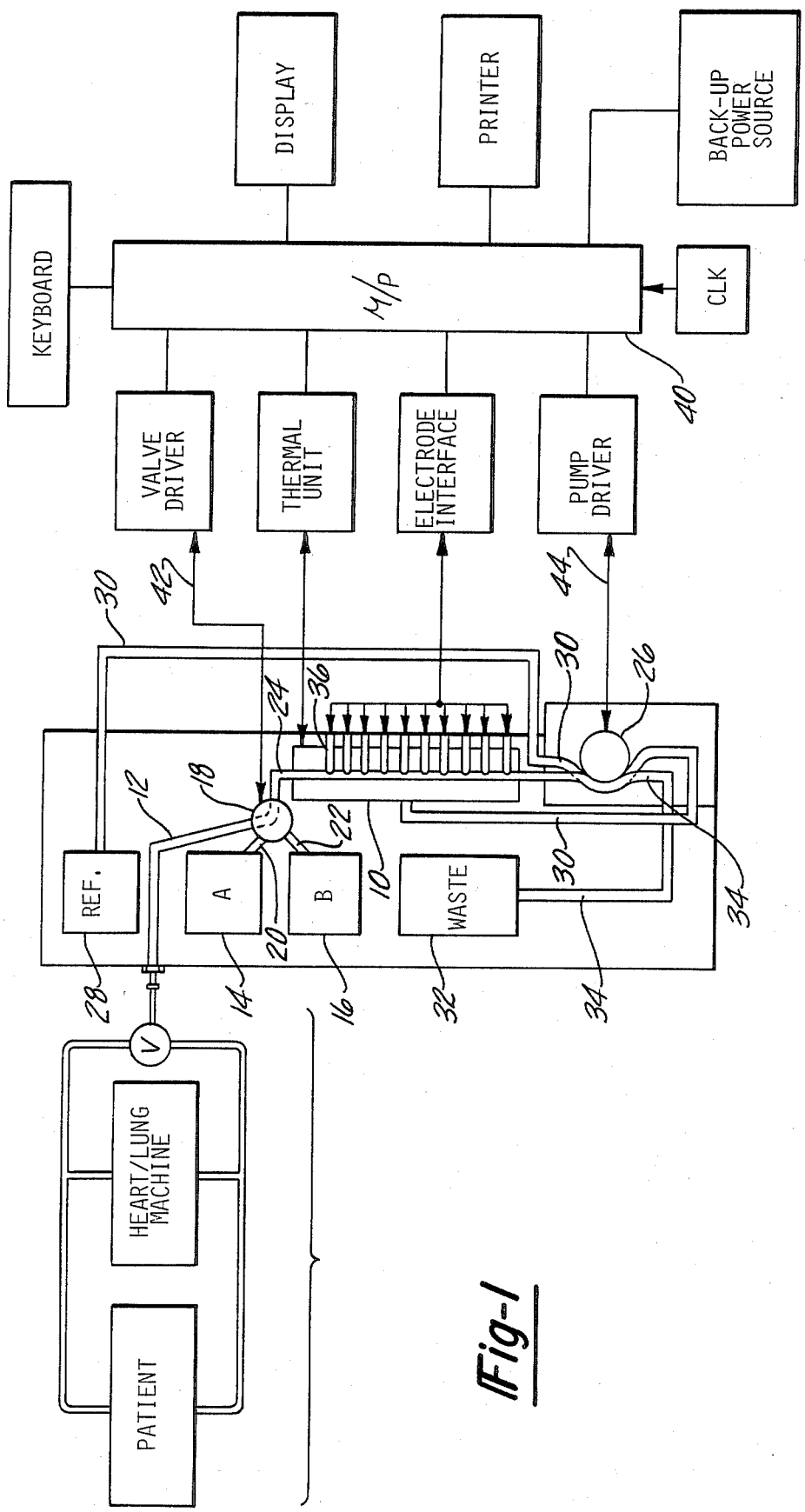
FIG. 1 is a schematic diagram showing the major components of a preferred embodiment of a blood gas analysis system.

Referring to FIG. 1, the overall system employs an electrode assembly, generally indicated at 10, incorporating a plurality of solid-state electrodes adapted to make electrical measurements on a blood sample introduced to the electrode assembly. Blood samples to be analyzed by the system are introduced through a conduit 12. These blood samples are preferably derived on a periodic basis from an extracorporeal blood flow circuit connected to a patient during open heart surgery. The nature of this extracorporeal circuit and the manner in which blood samples may be introduced into the analysis system of the present invention is disclosed in co-pending patent application Ser. No. 713,435, filed Mar. 19, 1985 and now abandoned, entitled "Apparatus For Chemical Measurement of Blood Characteristics", assigned to the assignee of the present invention and the disclosure of that co-pending application is incorporated herein by reference. Alternatively, blood samples may be introduced into the flow line 12 through other automatic means, or manually, as by syringe. The blood samples may be introduced as discrete samples, as described above.

The system incorporates two prepackaged containers 14 and 16 each containing calibrating aqueous solutions having known values of the parameters to be measured by the system. The two calibrating solutions have different known values of each of the measured parameters to allow the system to be calibrated on a 2-point basis. For purposes of reference the solution contained within the bag 14 will be termed Calibrating Solution A and the solution contained within the bag 16 will be referred to as Calibrating Solution B. Each of the bags 14 and 16 contains a sufficient quantity of its calibrating solution to allow the system to be calibrated a substantial number of times before the cartridge containing the containers must be replaced.

The container 14 is connected to the input of a 3-position valve 18 through a flow line 20 and the container 16 for calibration solution B is connected to a second input of the 3-position valve through a flow line 22. The blood sample flow line 12 is connected to the third input of the three-position valve. The valve 18 is adapted to connect one of the input flow lines 12, 20 or 22 to an output flow line 24, depending upon the position of the valve. The flow line 24 extends to the input of the electrode assembly.

The system includes a third container 28, for a reference solution. The container 28 is connected to the electrode assembly by a flow line 30. The system further includes a fourth container 32 for waste, which receives the blood samples, the calibrating solutions and the reference solution after they have passed through the electrode assembly 10, via a flexible conduit 34 that has input from the electrode assembly.

Both the waste flow conduit 34 and the reference solution flow line 30 consist of or include sections of flexible walled tubing that pass through a peristaltic pump, schematically illustrated at 26. The pump compresses and strokes the flexible sections of the flow lines 30 and 34 to induce a pressured flow of reference solution from the container 28 to the electrode assembly 10 and to create a negative pressure on the waste products in flow line 24 so as to draw fluids in the flow line 24 through passages in the electrode assembly 10. This arrangement, as opposed to the alternative of inducing positive pressure on the blood and calibrating solutions to force them through the electrode assembly 10, avoids the imposition of unnecessary and possibly traumatic mechanical forces on the blood sample and minimizes possibilities of leaks in the electrode assembly.

The system as heretofore described in a preferred embodiment of the present invention is contained in a disposable cartridge. A cartridge of a similar type is set forth in detail in the co-pending patent application referred to above. The present cartridge contains sufficient quantities of the calibrating solutions and the reference solution to perform analysis of a number of samples of blood. After use, the cartridge is intended to be discarded and replaced with another cartridge.

The electrode assembly 10 has a number of edge connectors 36 in a bank which allow it to be plugged into a female matching connector 38 so that the electrodes formed on the assembly 10 may be connected to an electronic controller 40. The electronic controller is connected to the valve 18 by a line 42 and to the motor of the peristaltic pump 26 by a line 44. The controller controls the position of the valve 18 and the energization of the pump 26 to cause sequences of blood samples and calibrating solutions to be passed through the electrode assembly. When the calibrating solutions are passed through the electrode assembly the electrodes forming part of the assembly make measurements of the parameters of the sample and the controller 40 stores these electrical values. Based upon measurements made during the passage of the calibration solutions through the electrode assembly, and the known values of the measured parameters contained within the calibrating solution, the controller 40 effectively creates a calibration curve for each of the measured parameters so that when a blood sample is passed through the electrode assembly 10 the measurements made by the electrodes can be used to derive accurate measurements of the parameters of interest. These parameters are stored and displayed by the controller 40.

The controller 40 preferably uses a suitably programmed microprocessor to perform measurement, calculation, storage and control functions, all as described in co-pending application referred to previously.

Calibrating Solutions

Containers 14 and 16 for the calibration solutions A and B respectively, are substantially identical and are prepared in the same manner. Each consists of an envelope formed by heat sealing together the edges of a pair of sheets of thin, flexible aluminum foil coated with plastic resins. The film material of the bags 14 and 16 must be substantially impervious to gases.

A preferred composition of calibrating solution A, prepared at 37° C. and at atmospheric pressure tonometered with 8% $CO_2$-$N_2$ gas, is as follows:

| COMPOUND | CONCENTRATION | MASS. 1.0 L |
|---|---|---|
| Buffer: Imidazole | 50 mmol/l | 3.405 g |
| $Na_2SO_3$ | 10 mmol/l | 1.260 g |
| $NaHCO_3$ | 11.5 mmol/l | 0.966 g |
| NaCl | 93 mmol/l | 5.44 g |
| $NaN_3$ | .01% w/w | .007 g |
| KCl | 2.0 mmol/l | .149 g |
| $CaCl_2.2H_2O$ | 0.25 mmol/l | .037 g |
| 1.0 N HCl | 23 mmol/l | 23 ml |
| 25 wt. % Surfactant (BRIJ 35) aq. soln. | 0.25 ml/l | |

This composition is effectively a blood facsimile and has the following parameters to be measured by the system:

| pH | $PCO_2$ mm Hg | $PO_2$ mm Hg | $K^+$-Radiometer | $K^+$-Nova | $Ca^{++}$ |
|---|---|---|---|---|---|
| 6.890–6.910 | 44–48 | 0.0 | 1.8–1.9 | 1.83–1.98 | .18–.22 |

A preferred composition for calibration solution B, prepared at 50° C. and at 700 mm. Hg absolute pressure tonometered with 21% $O_2$–4% $CO_2$-$N_2$ gas, is as follows:

| COMPOUND | CONCENTRATION | MASS. 1.0 L |
|---|---|---|
| Buffer, 3-Morpholinopropane-sulfonic Acid (MOPS) | 14.0 mmol/l | 2.926 g |
| Buffer, NaMOPS | 36.0 mmol/l | 8.316 g |
| Buffer, $NaHCO_3$ | 14.5 mmol/l | 1.218 g |
| NaCL | 110 mmol/l | 6.430 g |
| $NaN_3$ | .01% w/w | .007 g |
| KCl | 6.0 mmol/l | .447 g |
| $CaCL_2.2H_2O$ | 1.25 mmol/l | .184 g |
| 1.0 N HCl | ca 8 mmol/l | ca 8 ml |
| 25 wt. % Surfactant (BRIJ 35) aq. soln. | | |

The characteristics of calibration solution B as measured by the system are as follows:

| pH | $PCO_2$ mm Hg | $PO_2$ mm Hg | $K^+$-Radiometer | $K^+$-Nova | $Ca^{++}$ |
|---|---|---|---|---|---|
| 7.330–7.345 | 15.5–19.0 | 116–120 | 5.6–5.8 | 5.60–5.75 | .85–.95 |

The compositions of the two calibrating solutions are chosen so that for each of the characteristics measured by the system a pair of values are obtained that are spaced over the range of permissible values that are measured by the system, providing a balanced 2-point calibration for the instrument.

The calibration compositions are prepared by premixing all of the constituents, with the exception of the calcium dihydrate salt, next tonometering the solution with oxygen and $CO_2$ mixed with nitrogen to produce the desired level of pH for the solution; then adding the calcium salt; and finally retonometering the solution to adjust for any variation in the gas levels which occurred during addition of the calcium salt.

The temperature and pressure at which the calibrating solutions are prepared and their method of packaging must be such as to preclude the possibility of dissolved gases going out of solution in the container, which would affect the concentration of gases in the calibrating solutions, and to minimize the tendency for gases to permeate through even the most impermeable materials practically obtainable. The calibration solutions are packaged with the solutions completely filling the containers, so that there is no head space, by evacuating the containers prior to filling in a manner which will be subsequently described.

By filling the calibration solution into an evacuated flexible wall container at elevated temperatures and subatmospheric pressure, the solution will not have any tendency at a lower use temperature to outgas and thus produce gas bubbles in the container. Were outgassing to occur, the concentrations of the gases in the solution would be affected, creating an inaccuracy in the calibration of the instruments. Similarly, we have found that it is important that the calibration solutions not be packaged at too low a pressure i.e., not below about 625 mm of mercury, because the absorptive capacity of the solution for gases conceivably increases as the packaging pressure decreases and below that pressure value the absorptive capacity of the solution may be sufficiently high that it will tend to draw gases in through the slight inherent premeability of even the most gas impervious flexible packaging material, over long periods of time. Accordingly, a packaging pressure in the range of 625–700 mm of mercury is preferred.

It is also useful to prepare a calibrating solution at a temperature in excess of its intended use temperature so that at the lower temperature there is less tendency for outgassing of the dissolved gases. This cooperates with the reduced pressure packaging to minimize the possibility of outgassing.

Calibration Solution A is prepared at a temperature above its intended use temperature at a controlled pressure close to atmospheric pressure. This solution contains no oxygen. The sodium sulfite in the solution serves to remove any residual oxygen from the prepared solution. Through use of elevated temperature (e.g., 37° C.) the solution may be prepared at about atmospheric pressure without any possibility of subsequent microbubbles within the container or gas transfer through the container when packaged in a zero head space flexible gas impervious container.

The envelopes which form the calibration solution bags are formed of rectangular sheets, heatsealed at the edges and heatsealed at one corner to an inlet stem of the valve 18 which is used for filling purposes. In the preferred embodiment illustrated, the bags 14 and 16 and the bag stems 20 and 22 are formed in a unitary cluster with the valve 18 so that gas phase dead space in the tubing lines is thereby avoided. In a preferred procedure for purging and filling the envelope bags, the envelope is first evacuated and then filled with $CO_2$ gas. The $CO_2$ is then evacuated, the bag is filled with the prepared solution, and the solution is sealed in the container. This carbon dioxide gas purge cycle is performed, and repeated if necessary, so that gas, if any, left in the envelope during the final filling operation will be largely carbon dioxide. The calibrating solutions have a high absorptive capacity for carbon dioxide and accordingly any head space in the packages will be eliminated by absorption of the carbon dioxide after sealing of the packages. The bicarbonate-pH buffer systems of the calibration solution have a good buffering capacity for carbon dioxide so that the slight initial presence of gas phase carbon dioxide will not make any appreciable change in the concentration of carbon dioxide in the calibration solution.

The packaged calibration solutions have excellent stability and a long shelf life. When at use temperature and atmospheric pressure there is no possibility of any outgassing from the liquid to form gas bubbles within the container.

Reference Solution

The reference solution disposed in bag 28 is employed in the electrode assembly 10 as a supply source to a reference electrode to provide a liquid junction and thereby isolate the reference electrode from the varying electrochemical potential of the calibrating solution or the blood in a manner which will be subsequently described. In a preferred embodiment, the solution is 2 molar in potassium chloride solution and initially saturated with silver chloride. Thus, the reference solution is relatively dense compared to blood and calibration solution, being hypertonic. In other words, a density gradient exists between the reference solution and the less dense isotonic liquids. The solution also contains a surfactant such as Brij 35 (70 ul/l of solution, to minimize bubble formation) and sodium sulfite (0.16 molar). The sodium sulfite consumes any oxygen dissolved in the solution, keeping the solution unsaturated and thus preventing any formation of bubbles which would disrupt the operation of the device. The solution is prepared at room temperature and then cooled to a temperature below any reasonable storage temperature to allow the silver chloride to precipitate out. The solution is then filtered to remove the precipitate and is then packaged in a sealed flexible container with no head space. This technique assures that the concentration of silver chloride in the reference solution will be constant and independent of storage temperature.

Electrode Assembly

During operation of the pump 26, the electrode assembly 10 receives a constant pulsating flow of the reference solution via line 30 and sequential, intermittent pulsating flows of either the blood sample or one of the two calibrating solutions. The assembly also provides a corresponding output of its waste products to a waste collection bag 32 via line 34. The electrode assembly in a preferred embodiment consists of a structurally rigid rectangular plate or substrate 50 of polyvinylchloride having a rectangular aluminum cover plate 52 adhered to one of its surfaces. Cover plate 52 closes off the flow channels formed in one surface of the substrate 50 and also acts as a heat transfer medium to maintain the fluids flowing through the electrode assembly, and the electrodes themselves, at a constant temperature. As described in the above noted co-pending patent application, this may be achieved by measuring the temperature of the plate 52 and employing a suitable heating or cooling element to maintain the temperature of the plate at a constant desired level.

Figure 2:
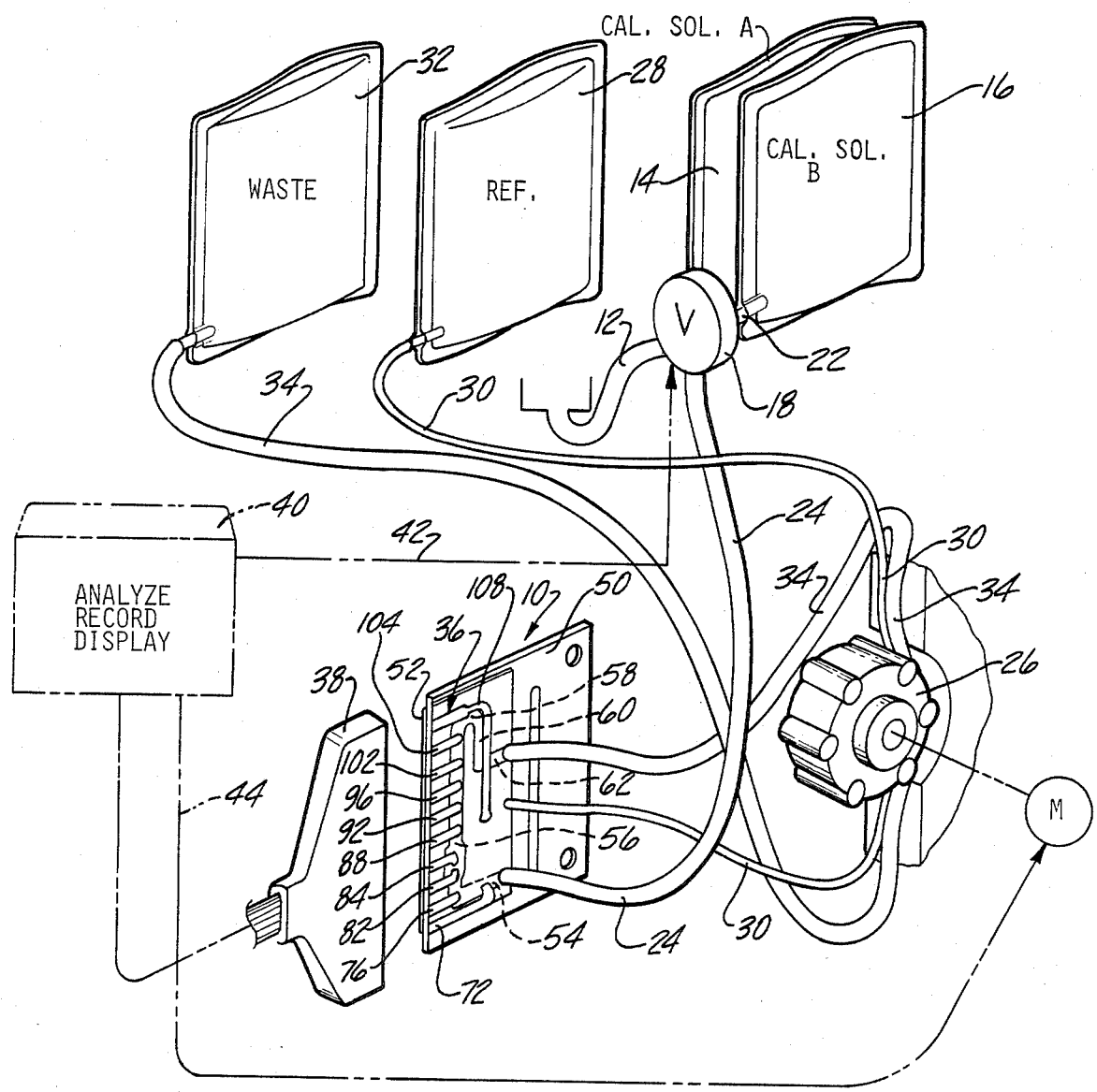
FIG. 2 is an exploded view of one embodiment of elements of a sampling cartridge useful with the system of FIG. 1.
Figure 6:
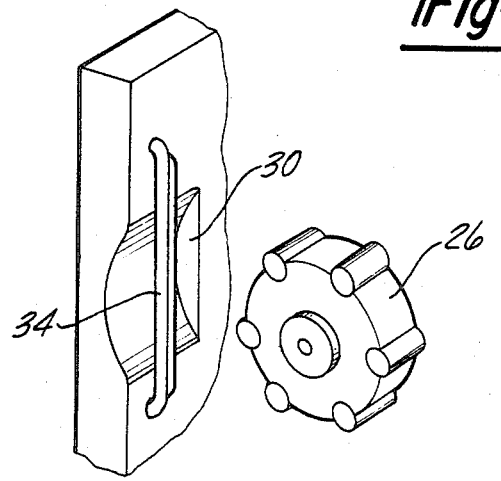
FIG. 6 is a fragmentary side view of the end wall at the insertion end of this embodiment of the cartridge, showing the peristaltic pump slot.
Figure 3:
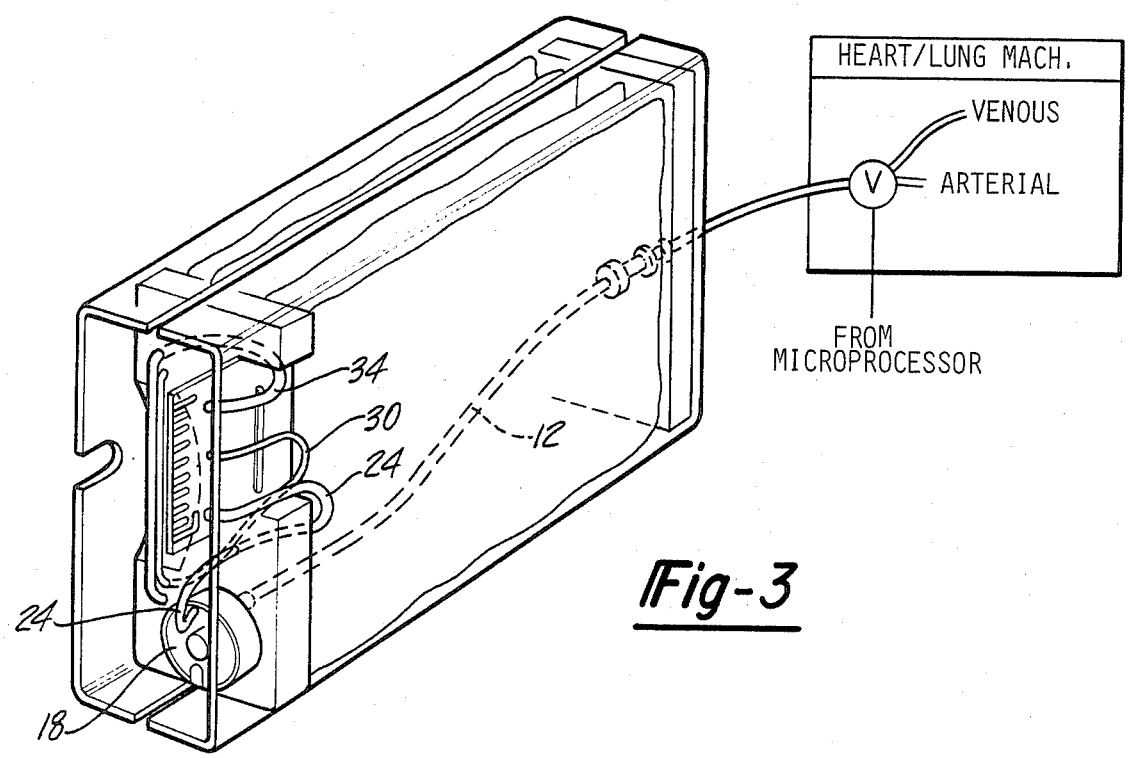
FIG. 3 is an elevated side view of this embodiment of the cartridge showing the insertion end of the cartridge in the foreground.
Figure 4:
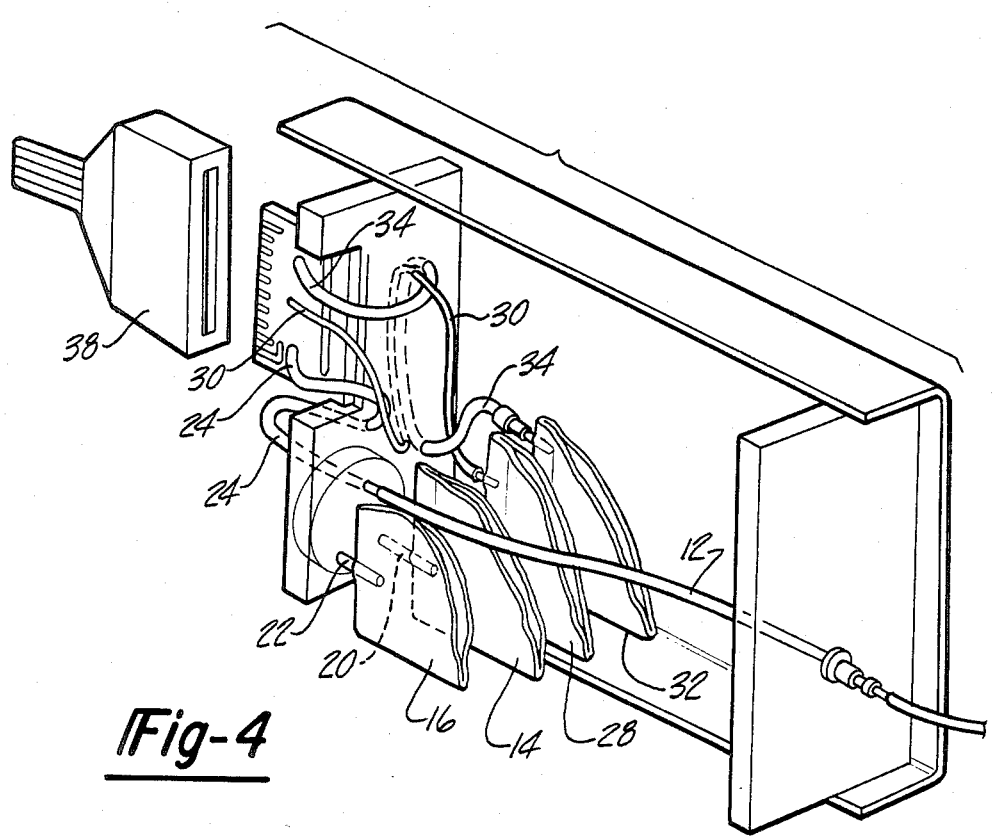
FIG. 4 is a fragmentary side view of the trailing end of this embodiment of the cartridge.
Figure 5:
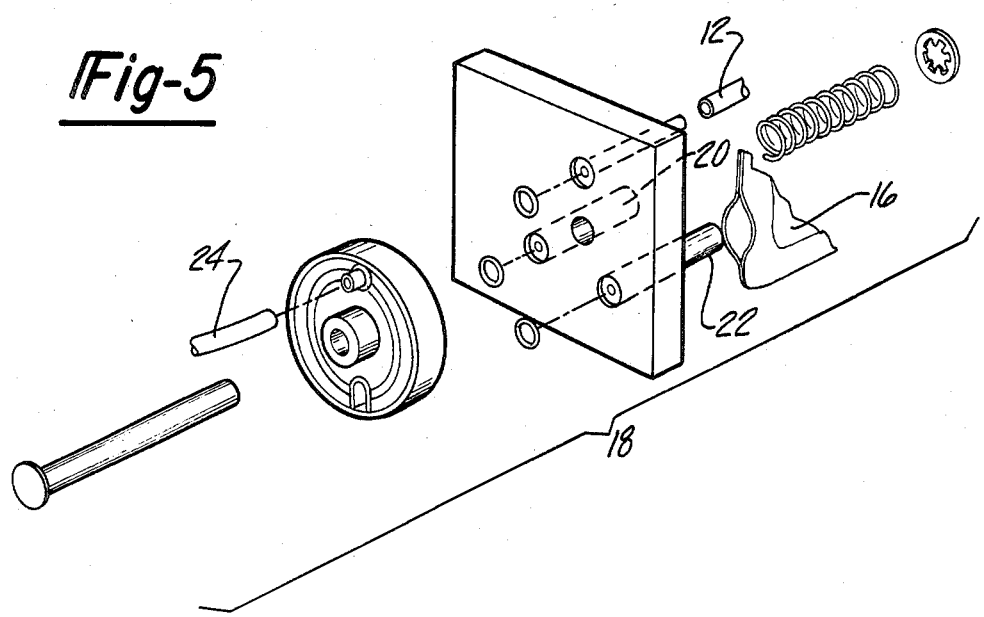
FIG. 5 is an exploded view of the selection valve contained in this embodiment of the cartridge.
Figure 8A:
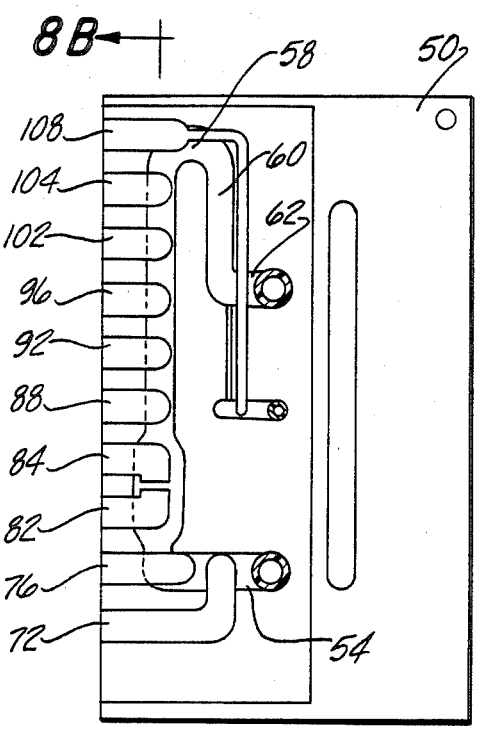
FIG. 8a is a frontal view of the electrode card contained in this embodiment of the cartridge.
Figure 8B:
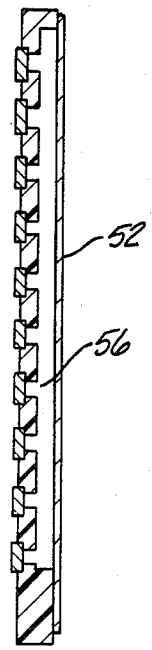
Figure 7:
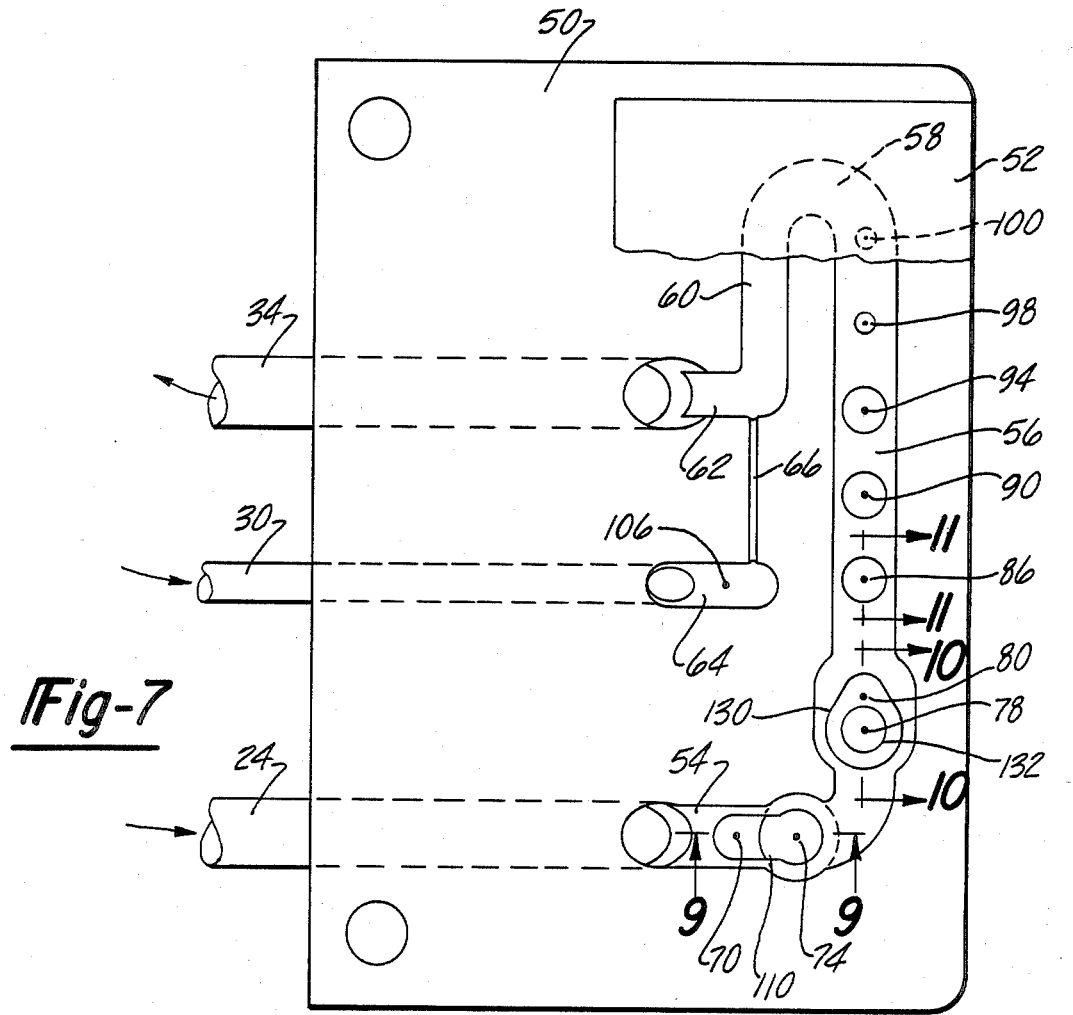
FIG. 7 is a reverse frontal view of the electrode card, partly fragmentary, contained in this embodiment of the cartridge.

The rectangular electrode assembly is intended to be used with its major surfaces and its major axis in the vertical plane (FIG. 7) and is so supported. The flow line 24 from the valve 18 passes through the thickness of plate 50 from the side opposite to the plate 52, near the bottom of the plate 50, at an angle (FIG. 2) with respect to the plates, to communicate with a horizontal flow channel 54 formed in suitable manner (e.g., machined, molded, or etched) in the surface of the plate 50 that abuts the cover plate 52, so that the abutting surface of the plate 52 forms one wall of the flow channel. Near one long edge of the plates 50 and 52 the horizontal flow channel 54 turns upwardly into a main flow channel 56 (FIG. 8B) which extends parallel (FIG. 8A) to the one long edge of the plates 50 and 52. Near the upper edge of the plate 50 the flow channel 56 makes a hair pin (180°) bend inwardly, away from the edge of the plate, at 58 to form a downwardly extending section 60 parallel to and spaced from the main flow channel 56. At its lower end, about ⅓ of the way from the top of the plate, the channel 60 makes a 90° turn to join with a short horizontally extending section 62. The waste flow line 34 passes through the thickness of the substrate 50 from the side opposite to the cover plate 52 to communicate with the end of the flow channel 62. Thus, blood samples or calibrating solution, pumped into the electrode assembly via line 24, move horizontally along flow channel section 54, then upward vertically through the flow channel section 56, then around the curve of the section 58 at the top of the assembly, down the section 60, and finally horizontally along the section 62 to the output flow line 34 which carries the used fluids to the waste bag 32.

The provision of a main flow channel in which the blood and calibrating solutions must flow vertically upward ensures that any microbubbles in the blood or calibrating solution will rise to the space at the top of the main flow channel and not interfere with accurate measurements made by the electrodes.

The reference solution is introduced to a well 64 (FIG. 7), formed in the surface of the substrate 50 in the same manner as the other flow channels and similarly covered by the metal plate 52. The reference solution flow line 30 passes through an inclined hole in the well 64. The well 64 is connected to the output section 62 of the flow channel through a very thin capillary section 66 formed in the surface of the plastic substrate 50 in the same manner as the main flow channels. The capillary channel 66 is straight and substantially shallower and narrower than the main flow channel; its cross section is approximately 0.5 sq. mm. Reference fluid pumped into the well 64 by the pump 26, via a line 30, fills the well, and is forced through the capillary section 66 where it joins the output stream of fluid passing through the main flow channel section and then flows with it to the waste bag 32. The combined influence of its higher density described above and the capillarity of the flow channel 66 serves to minimize any possibility of calibrating solution or blood passing downward through the channel 66 to the wall 64 and upsetting the electrochemical measurements.

As a blood sample or calibration solution quantity introduced into the flow channel 54 passes through the flow channel to the output section 62, it passes over a number of solid-state electrodes.

The Oxygen Electrode Pair

The first of these electrodes (FIG. 9) along the flow path is a silver wire 70 which constitutes a reference half of an oxygen electrode. The silver wire 70 is preferably approximately 15 mils in diameter and is staked through the thickness of the plastic plate 50 from the side opposite to the cover plate 52 into the bottom of the flow channel 54. A silk screen printed conductor section 72, formed on the side of the substrate 50 opposite to the flow channel (FIG. 8A) connects the end of the silver wire 70 to the edge of the plastic plate, to act as one conductor of the edge connector.

The next electrode up the flow channel is the active part of the oxygen electrode comprising wire electrodes 70 and 74, which will be subsequently described in detail. Printed circuit sections 72 and 76 form the edge connection for these oxygen electrodes. Both electrodes are covered by hydratable membranes 112 and 114.

The Carbon Dioxide Electrode Pair

The next electrode (FIG. 10) along the flow channel makes a measurement of the dissolved carbon dioxide in the blood or calibrating solution and employs a pair of silver wires 78 and 80 staked through the thickness of the plastic substrate to the flow channel and joined by silk screen printed circuit elements 82 and 84 which act as edge connectors. These electrodes are covered by hydratable membranes 135, 138, 142, 144 and 148. The nature of the $CO_2$ electrode will be subsequently described in detail.

The pH Electrode

Next along the flow channel is a pH sensing electrode (FIG. 11) which includes a membrane 148 and a silver wire 86 staked or press-fitted through the thickness of the plastic into the flow channel and joined on the opposite side of the flow channel by a silk screen printed conductor section 88 to form an edge connector. The nature of this pH electrode will be subsequently described in detail.

The Potassium Ion Sensing Electrode

Next up the flow channel is a potassium sensing electrode (of the type shown in FIG. 11) including an active membrane and a staked silver wire 90 and an associated edge connector 92.

The Calcium Ion Sensing Electrode

Next is a calcium sensing electrode (of the type shown in FIG. 11) including an active membrane and a staked wire 94 and an associated printed circuit connector 96.

The Hematocrit Electrode Pair

Finally a pair of silver wires 98 and 100 form electrodes for determining the hematocrit (Hct) of a sample based on its conductivity. The wires make contact with printed circuit edge connectors 102 and 104 respectively. One of the hematocrit pair 98 and 100 also completes the electrical circuit for the measurement of pH, potassium and calcium potentials along with the reference potential, using electrodes 86, 90, 94, and 106, respectively.

The Reference Electrode

Finally, a silver wire 106 (FIG. 7) is staked through the thickness of the plastic board 50 into the reference solution well 64 to act as a reference electrode, which has its circuit completed by the same member of the hematocrit pair that grounds the ion sensing electrodes. A printed circuit element 108 extends along the back of the panel between the one end of this reference electrode and edge of the board to provide an edge connector.

The specific construction and operation of the electrodes will now be described in detail.

SPECIFICS OF THE $PO_2$ ELECTRODE

Figure 9:
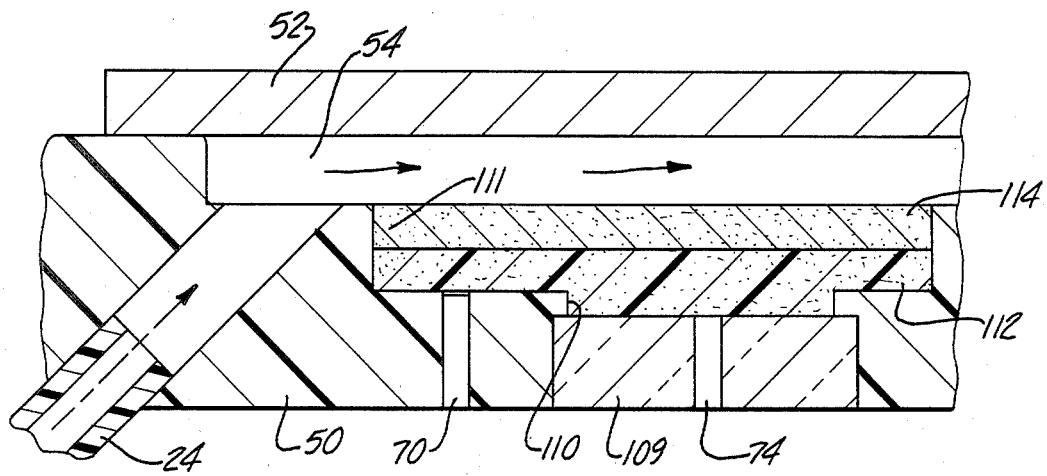
Figure 12:
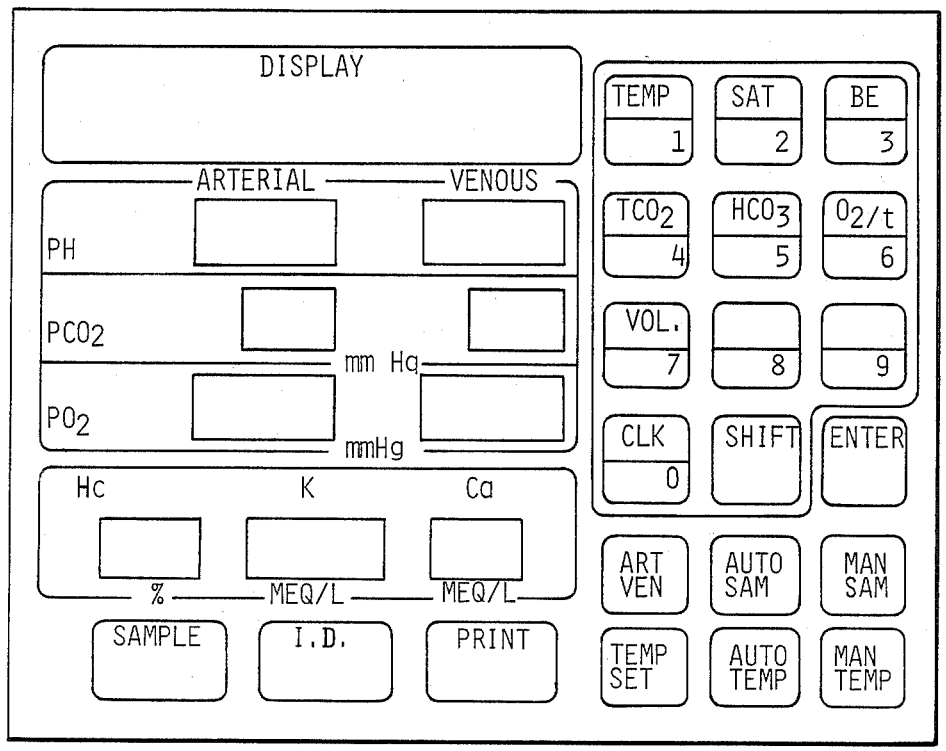
FIG. 12 is a frontal view of one embodiment of the control panel of the blood gas analysis machine showing the display and keyboard.

The platinum wire 74 forming part of the oxygen electrode is fixed in the center of an insulative glass disk 109 best shown in FIG. 9. The disk preferably has a thickness of approximately 40 mils while the board 50 may have a thickness of approximately 85 mils. The diameter of the glass disk is preferably about 100 mils.

A number of the glass disks with the embedded platinum wires are prepared by inserting a close-fitting length of platinum wire into the capillary of a glass capillary tube and then melting the tube so that it fuses to the wire. After the tube with the embedded wire hardens, the disks of given axial thickness are sliced off, e.g., by power saw means.

The glass disk is embedded in a recess formed through the thickness of the plastic board 50 so that one surface is flush with the surface of the board opposite to the cover plate 52 and the outer surface of the disk abuts a shoulder 110 formed around the bottom of the flow channel.

The glass disk is practically impervious to oxygen whereas the polyvinylchloride of the board 50 is relatively pervious. The glass disk thus protects the platinum electrode 74 from the gas so that only its distal end that faces the flow channel is active.

The upper surface of the silver electrode 70 is coated with a thin film of silver chloride preferably by filling the well with a potassium chloride solution and passing an electric current through the solution and electrode to plate or anodize a thin film of silver chloride on the electrode end.

The flow channel section 54 is depressed or increased in depth in the area of the oxygen electrode elements 70 and 74 to form a well 111. In fabricating the electrode, the glass disk 109 is inserted in place against the shoulder 110 and a two layer permeable membrane (covering the glass disk) is formed in the well so that its upper surface is substantially flush with the flow channel. The bottom hydratable layer 112 which is a critically important layer is a dried or substantially dried residue remaining after solvent removal from, or dehydration of, a solution of a hygroscopic electrolyte. The membrane may be conventional in this regard and may use known components (such as hydrophilic polymeric film-forming materials) and methods of preparation. The membrane is a hydratable membrane as broadly defined by Battaglia et al., U.S. Pat. No. 4,214,968, incorporated by reference herewith. A preferred and novel hygroscopic electrolyte for the hydratable layer is a dried residue remaining after solvent removal from an aqueous solution comprising hydratable saccharide or polysaccharide and an electrolyte such as KCl. For best results, one uses a solution of hydratable saccharide and potassium chloride, preferably a small amount of sucrose (e.g., 0.6 g.) in 4.4 ml. of 0.0005M aqueous potassium chloride or an approximation or equivalent of such solution. This aqueous solution is dispersed into the well as a layer and the layer is allowed to desiccate or dry to form a dehydrated thick film. After this bottom layer 112 dries, the upper, water-and-gas permeable hydrophobic layer 114 is formed, using a film-formed polymeric membrane binder as defined by the patent of Battaglia et al. For best results, this is done by introducing a permeable hydrophobic membrane forming solution, preferably a solution of a polymer such as polyvinylchloride, a suitable plasticizer such as bis(2-ethylhexyl)phthalate, and a solvent, preferably tetra-hydrofuran (THF). The solvent is then removed. When and as the solvent evaporates, a residual membrane is formed that is permeable to oxygen and water. In use, for equilibrium, when a calibrating solution is made to dwell in the channel, water passes by permeation through the upper layer 114 to the lower layer 112 where it causes hydration of the lower layer 112 to form an aqueous solution. This hydration process from a non-conductive dry state to an electrochemically conductive stabilized hydrated state, typically requires a short start-up period to reliably achieve reproduceable hydration of the lower layer.

Concerning the amperometric function of the electrode in operation, negative potential relative to the silver electrode 70 is applied to the platinum wire 74 by the controller 40 which lessened potential serves to reduce any oxygen reaching its end and thereby produces an electrical current proportional to the oxygen diffusion through the layer 112. The hydrated layer 112 affords a reproduceably reliable conductive flow path between the platinum electrode and the silver electrode 70 to provide a polarization potential between the platinum and the solution in the hydrated layer. The resulting current flow is measured and is proportional to the oxygen concentration in the test fluid being monitored.

Advantageously, since the active layer is dehydrated prior to use, the electrode (either alone or in an assembly with other electrodes as in a bank or cartridge bank) can be stored indefinitely. Unlike conventional Clark electrodes and of major importance, the electrode is inactive until required and is then self-activating such that under normal use conditions in the water contained in the equilibrating/calibrating solution, the permeability of its upper layer to water allows water thus permeating to cause hydration of the lower level to render it fully and reproduceably active. This solid state electrode structure is also advantageous when compared to the conventional Clark electrode in that it does not require an assembly of discrete mechanical components. It is a durable, single solid state pre-assembled structure that is inherently small in size, inexpensive to manfacture, and requires no maintenance.

SPECIFICS OF THE $pCO_2$ ELECTRODE

Figure 10:
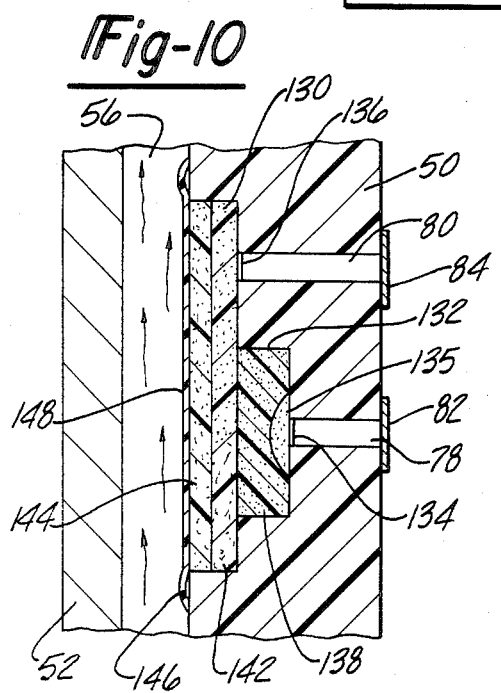
FIGS. 9, 10 and 11 are sectional views taken respectively on line 9—9, line 10—10 and line 11—11 of FIG. 7.

The carbon dioxide electrode utilizing the silver wires 78 and 80, illustrated in cross-section in FIG. 10, is formed within a double depth (or double bore) depression comprising larger and smaller bores in the flow channel 56. The flow channel is also widened at the area overlying the silver wires 78 and 80. A preferred normal width of about 80 mils is increased at the section overlying $CO_2$ electrode to a width of about 100 mils. The larger or outer depression 130 is generally oval shaped and is preferably about 1 mil deep below the normal bottom of the flow channel. It has a central counter-bore 132 which is preferably 5 mils in depth. The active electrode wire 78 extends into the central counter-bore 132, and the reference silver wire 80 extends into the outer depression 130. The upper surfaces of both the wires 78 and 80 are coated with a thin film of silver chloride in the same manner that the silver electrode 70 is coated. The silver chloride thin film layer on the electrode 78 is identified as 134 while the silver chloride thin film layer at the end of the electrode 80 is denominated 136.

Within the central well 132, over the silver chloride thin film 134, is a small diameter water permeable hydrophobic membrane or bead 135 formed as a dry residue remaining after solvent removal from a solution of a permeable hydrophobic membrane forming solution, preferably a solution containing polyvinylchloride (PVC), a plasticizer such as bis (2-ethylhexyl)sebacate, an ion sensitive active ingredient (preferably tridodecylamine, TDDA), and potassium chloride in water. The dry membrane or bead 135 is completely covered with a pH sensitive layer or membrane 138 formed as a dry residue remaining after solvent removal from a matrix of a permeable hydrophobic membrane forming solution, preferably PVC, PVC plasticizer such as bis (2-ethylhexyl) sebacate, TDDA, and a solvent such as THF.

The bottom of the larger well area 130 contains a hydratable membrane layer 142 which is a critically important layer. The layer is a dried or substantially dried residue remaining after solvent removal from, or dehydration of, an aqueous solution of a hygroscopic electrolyte (as defined above) that is buffered. A preferred and novel electrolyte for the purpose is a dried residue remaining after solvent removal from an aqueous solution comprising hydratable saccharide, potassium chloride, and sodium bicarbonate, preferably an aqueous solution of sucrose, potassium chloride and sodium bicarbonate. This layer 142 is covered by an upper layer 144 which is a permeable hydrophilic material, preferably of a polyvinyl alcohol matrix (PVA, KCl, $NaHCO_3$) put down in a water solvent and allowed to dry. These two layers 142 and 144 are covered by a permeable hydrophobic membrane 149, and the latter may be held in place by a bead 146 of a suitable adhesive such as cyanoacrylate adhesive joining the membrane to the margins of the polyvinyl chloride well. The permeable membrane 149 is suitably prepared by drying a liquid film formed from a mixture of polyvinylchloride, a PVC plasticizer and a solvent such as THF, which layer is fused to the plate 50.

The hydrophobic and hydrophilic layers 148 and 144 are permeable to water and they effectively serve as a selective conduit to allow the water to permeate layers 138, 142 and 144. The silver/silver chloride layer 134 forms a reversible electrochemical couple with layer 135 which latter layer absorbs water through its interstices but does not hydrate. Accordingly the physical form of layer 135 does not appreciably change as it absorbs and loses water so that it does not deleteriously affect the relatively fragile, overlying protective thin film membrane structure.

Concerning the potentiometric function in operation, the $CO_2$ electrode senses dissolved $CO_2$ by sensing changes in pH in the hydratable layer 142 which changes are a function of the transient changes in the carbon dioxide level as defined by the Henderson-Hasselbalch equation (cf. Page 893, Fundamentals of Clinical Chemistry, supra). The potential that exists between electrodes 78 and 80 is measured by the controller 40 and is proportional to the carbon dioxide activity of either the blood or the calibrating solution in the flow channel.

The concept of having a water and gas pervious layer covering a hydrating layer which in turn covers a reversible electrochemical couple which again in turn absorbs water, is a broadly important improvement over conventional Stow-Severinghaus electrodes.

Like the present oxygen electrode, this $CO_2$ electrode is simple in construction, low in cost, durable, compact and reliable in operation. The electrode is superior in these respects to the conventional Stow-Severinghaus electrodes. The latter are formed with discrete components, mechanically assembled, and require final assembly by the end user.

ION SENSING ELECTRODES

Figure 11:
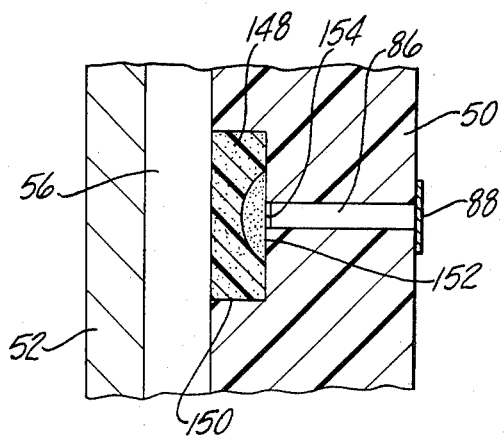

The electrodes connecting to the silver wires 86, 90 and 94 which sense pH, potassium and calcium activities, respectively, are similar in construction to the bottom layers of the $CO_2$ electrode. The electrodes differ only in the nature of their ion sensitive active ingredient. The pH electrode illustrated in FIG. 11 is typical. Each has a bead or lower layer 152 (layer No. 1) and an upper layer 148 (layer No. 2). The upper layer is comparable to layer 138 of the $CO_2$ electrode, formed in a shallow well 150 as a dry residue remaining after solvent removal from a matrix of a permeable hydrophobic membrane forming solution such as a solution consisting of polyvinylchloride, PVC plasticizer, a solvent and an appropriate ion sensitive active ingredient. In the case of the pH electrode, the ion-selective active ingredient may be tridodecylamine (TDDA) or other suitable pH sensing component. For the potassium electrode, a macrocyclic antibiotic such as valinomycin or other suitable kalliphylic substance may be the active ingredient. The calcium electrode employs a calcium ion-selective sensing component as its active ingredient such as 8,17-dimethyl-8,17-diaza-9,16-dioxo-11,14-dioxa-tetracosane, or other suitable calcium sensitive selector substance. As indicated, each of these layers covers a bead 152, comparable to layer 135 of the $CO_2$ electrode, formed as a dry residue remaining after solvent (e.g., THF) removal from a permeable hydrophobic membrane forming solution, preferably a solution containing polyvinylchloride, a plasticizer, the ion sensitive active ingredient and appropriate electrolyte salt solution such as potassium chloride in water for the potassium-sensing electrode. This is in contact with the thin film silver/silver chloride layer 154 anodized onto the top of a silver wire 86.

The controller measures the potential difference between the silver wire forming part of each of these electrodes and one of the two wires 98 or 100. It also measures the potential between that wire 98 or 100 and the reference electrode 106 and subtracts the voltage with respect to the reference electrode from the voltage with respect to the active electrode to arrive at a voltage value proportional to the measured ion.

Layer 152 of these ion sensing electrodes provides the same advantages with respect to the prior art as does layer 135 of the $CO_2$ electrode. Thus, it absorbs water without structural deformation or phase change. It absorbs the water rather than creating an independent water layer. It does not undergo any appreciable changes as it absorbs and dries out as do the prior art structures. It is also compact and inexpensive to fabricate.

Hematocrit Measurement

The hematocrit (Hct) measurement is achieved as a measurement of resistivity between silver wires 98 and 100. As has been noted, one of these wires also acts as a grounding electrode for the ion and reference measurements.

Reference Solution Operation

As has been noted, the reference solution fills the well 64 where it contacts a silver wire 106 and is pumped through the capillary channel 66 to join the outlet of the main flow line. The reference solution is essentially a hypertonic solution of potassium chloride, with respect to the blood or the calibrating solutions and accordingly the domain of the reference electrode 106 constitutes a stable potential liquid junction formed between the reference electrode and the blood or calibrating solution, thereby establishing an environment that is independent of the ionic activity of the blood or calibrating solution.

Since the reference solution joins the main flow channel downstream from the electrodes, after the gas/electrolyte measurements have been made, it does not affect those measurements in any way. The reference solution is of high density and under pumping force must flow upward against gravity to the outlet. Thus, when the pump stops, as for electrode equilibration, the reference solution remains stationary in the reference well 64 and the capillary section 66 and tends not to diffuse into the calibrating solution or blood in the main flow channel. Thus, the capillary tube 66 due to the density gradient, acts as a one way valve allowing pumped reference solution to pass upwardly through the capillary but preventing unwanted reverse passage or mixing of the blood or calibrating solution into the reference well.

Assembly Operation

When the sensor assembly 10 and the filled bags 14, 16 and 28 of calibration solution 14 and 16 and reference solution are first used, the valve 18 is controlled to direct one of the calibration solutions into the sensor assembly so it entirely fills the flow channel and is void-free. The pump is then stopped for a period (e.g., 30 minutes) during which the electrodes are allowed to stabilize in the electrode solution. After the stabilization, a predetermined quantity of new calibration solution A is pumped into and through the sensor assembly and during a dwell period (e.g., 90-second dwell) measurements of the various potentials and currents are made and processed by the controller. Next, a predetermined quantity of calibration solution B is pumped into and through the sensor card while, during a like dwell, similar measurements are made. The blood sample from line 12 is then pumped into the card while analogous measurements are made and, based on the measurements of the blood sample and the stored measurements, the controller, with suitable allowance permitted by 2-point calibration, generates the gas/electrolyte values characteristic for the particular blood sample.

This process may be repeated a number of times, either automatically or manually using discrete blood samples under operator control, all within the operating theater or at bedside, to derive quantitative parameters for any of a series of blood samples over a period of time, until the solutions have been depleted, at which time the spent cartridge can be discarded and replaced with a fresh one.

Preferred solutions for fabricating the above-identified electrodes have, as an illustration of the best mode, the following compositions, in which the component quantities are expressed as grams (g), milliliters (ml), and microliters (ul):

| $O_2$ Electrode Layer Compositions | |
|---|---|
| Sucrose Layer Composition | |
| Sucrose | 0.6 g |
| 0.0005 M KCl | 4.4 ml |
| $O_2$ Outer Membrane Composition | |
| Polyvinyl chloride | 0.2 g |
| Bis (2-ethylhexyl) phthalate | 220 ul |
| Tetrahydrofuran | 6.0 ml |
| $CO_2$ Electrode Layer Compositions | |
| Sucrose/Bicarb Layer Composition | |
| Sucrose | 0.6 g |
| 0.0005 M KCl | 4.4 ml |
| 0.00015 M $NaHCO_3$ | |

This is an aqueous solution prepared with the specified composition and used in the amount indicated.

| Polyvinyl Alcohol/Bicarb Layer Composition | |
|---|---|
| Polyvinyl Alcohol | 0.1 g |
| 0.0005 M KCl | 4.9 ml |
| 0.00015 M $NaHCO_3$ | |
| $CO_2$ Outer Membrane | |
| Polyvinyl Chloride | 0.2 g |
| Bis (2-ethyl hexyl) sebacate | 220 ul |
| Tetrahydrofuran | 6 ml |

Note:
The pH portion of the $CO_2$ electrode uses the same solutions as in the pH electrode. The adhesive in the $CO_2$ electrode is cyanoacrylate adhesive (Loctite 416).

| Potassium Electrode Internal Solution Composition | |
|---|---|
| Polyvinyl Chloride | 0.2 g |
| Valinomycin | 0.0062 g |
| Bis (2-ethyl hexyl) sebacate | 440 ul |
| Tetrahydrofuran | 3.0 ml |
| 0.0001 M KCl | 100 ul |
| Potassium Electrode Ionophore Solution Composition | |
| Polyvinyl Chloride | 0.2 g |
| Valinomycin | 0.0062 g |
| Bis (2-ethyl hexyl) sebacate | 440 ul |
| Tetrahydrofuran | 3.0 ml |
| Calcium Electrode Internal Solution Composition | |
| Polyvinyl Chloride | 0.2 g |
| Potassium tetrakis (4-chlorophenyl) borate | 0.0126 g |
| Bis (2-ethylhexyl) sebacate | 435 ul |
| Neutral Carrier ETH 1001 | 0.0215 g |
| Tetrahydrofuran | 3.0 ml |
| 0.0001 M $CaCl_2$ | 100 ul |
| Calcium Electrode Ionophore Solution Composition | |
| Polyvinyl Chloride | 0.2 g |
| Potassium tetrakis (4-chlorophenyl)borate | 0.0126 g |
| Bis (2-ethylhexyl) sebacate | 435 ul |
| Neutral carrier ETH 1001 | 0.0215 g |
| Tetrahydrofuran | 3.0 ml |
| Hydrogen Electrode Internal Solution Composition (Layer #1) | |
| Polyvinyl Chloride | 0.2 g |
| Potassium tetrakis (4-chlorophenyl)borate | 0.004 g |
| Tridodecylamine | 8 ul |
| Bis (2-ethyl hexyl) sebacate | 440 ul |
| Tetrahydrofuran | 3.0 ml |
| 0.0001 M KCL | 100 ul |
| Electrode Ionophore Solution Composition (Layer #2) | |
| Polyvinyl Chloride | 0.2 g |
| Potassium tetrakis (4-chlorophenyl)borate | 0.004 g |
| Tridodecylamine | 8 ul |
| Bis (2-ethyl hexyl) sebacate | 440 ul |
| Tetrahydrofuran | 3.0 ml |

The embodiments of the invention in which an exclusive property or privilege is claimed are defined as follows:

We claim:

1. An electrode assembly comprising:
a planar base member;
an elongated flow channel formed partially through the depth of the base member and opening to one surface thereof;
a plate member fixed to the surface of the base member which has the flow channel formed therein to close off the open side of the flow channel;
a first well of increased depth relative to the depth of the flow channel, formed in the base member along a portion of the length of the flow channel;
a second well of increased depth relative to the depth of the first well formed in the base member along a portion of the length of the first well;
an outer, planar, gas and water permeable, hydrophobic membrane layer formed over the entire surface of the first well and contacting the edges of the flow channel adjacent the first well so as to effectively form a portion of the wall of the flow channel over the first well;
an intermediate, planar, gas and water permeable, hydrophilic electrolyte membrane layer containing a pH buffer underlying the outer planar membrane, within the first well;
an inner, planar gas and water permeable hygroscopic electrolyte membrane layer conaining a pH buffer underlying the intermediate layer within the first well;
a conductive reference electrode passing through the thickness of the base member from the side opposite that containing the first well, at a point spaced from the second well, having one end in conductive contact with the underside of said inner planar electrolyte layer;

a conductive active electrode extending through the thickness of the base from the side opposite to that containing the wells at the area of the second well, so that one of its ends extends to the second well;

an active, inner, water permeable, electrolyte layer formed within the second well with one of its surfaces in contact with the active electrode surface which extends to the second well;

an active, outer, water permeable, polymeric pH sensitive layer filling the remaining volume of the second well so as to contact said active inner electrolyte layer and said inner planar hygroscopic electrolyte layer contained within the first well;

means for introducing aqueous fluid samples into the flow channel for measuring the content of carbon dioxide gas dissolved in the fluid; and signal receiving means adopted to be connected to the ends of the active and reference electrodes opposite to the ends of those electrodes contacting the electrolyte layers;

whereby the assembly, when hydrated by an aqueous fluid sample, is capable of electrochemical interaction with the carbon dioxide content of an aqueous fluid sample such that an electric potential difference is generated between said electrodes as a function of the carbon dioxide content, for measurement by said signal receiving means.

2. An electrode assembly according to claim 1 where the reference electrode and the active electrode each have contact with the respective inner electrolyte layers through an electrode coupling surface.

3. An electrode assembly comprising:

a fluid flow channel;

a first outer, planar, gas and water permeable, hydrophobic member layer forming a poriton of the wall of said flow channel;

a second, intermediate, planar, gas and water permeable, hydrophilic electrolyte membrane layer containing a pH buffer in contact with said first membrane layer on the side opposite said flow channel;

a third, inner, planar, gas and water permeable hydroscopic electrolyte membrane layer containing a pH buffer in contact with at least a portion of said second membrane layer on the side opposite said first layer;

a conductive reference electrode having one end in contact with said third membrane layer;

a fourth, active, water permeable, polymeric, pH sensitive layer in contact with a portion of the surface of said third membrane layer opposite to the surface of that layer which is in contact with said second membrane layer;

a fifth, active, inner, water permeable electrolyte layer disposed in contact with a portion of the surface of said fourth layer;

a conductive active electrode having one end in contact with said fifth layer;

means for introducing aqueous fluid samples into the flow channel for measuring the content of carbon dioxide gas dissolved in the fluids; and signal receiving means adapted to be connected to the ends of the active and reference electrodes opposite to the ends of those electrodes contacting the electrolyte layers for receiving and analyzing electrical signals;

whereby the assembly, when hydrated by an aqueous fluid sample, is capable of electrochemical interaction with the carbon dioxide content of an aqueous fluid sample such that an electric potential difference is generated between said electrodes as a function of the carbon dioxide content, for measurement by said signal receiving means.

4. The electrode assembly of claim 3 further including means for containing a calibrating facsimile fluid, and means for sequentially directing first said facsimile fluid and then said aqueous fluid sample through the flow channel, such that, during the time that the facsimile fluid is disposed in the flow channel the electrode assembly layers become hydrated and the signal sensing means receives a potential difference useful in calibrating the assembly for subsequent measurement of the carbon dioxide content of the fluid sample, when said fluid sample is in the flow channel in association with the still hydrated electrode assembly.

5. An electrode assembly according to claim 2 where the reference electrode and the active electrode each have contact with the respective inner electrolyte layers through an electrode coupling surface.

* * * * *